US008012742B2

(12) United States Patent
Haubert et al.

(10) Patent No.: US 8,012,742 B2
(45) Date of Patent: Sep. 6, 2011

(54) BUFFY COAT TUBE AND FLOAT SYSTEM AND METHOD

(75) Inventors: Thomas Haubert, Columbus, OH (US); Stephen C. Wardlaw, Highrock, CT (US)

(73) Assignee: Battelle Memorial Institute, Columbus, OH (US)

( * ) Notice: Subject to any disclaimer, the term of this patent is extended or adjusted under 35 U.S.C. 154(b) by 0 days.

(21) Appl. No.: 13/052,151

(22) Filed: Mar. 21, 2011

(65) Prior Publication Data

US 2011/0171680 A1 Jul. 14, 2011

Related U.S. Application Data

(60) Continuation of application No. 12/029,274, filed on Feb. 11, 2008, now Pat. No. 7,915,029, which is a continuation of application No. 11/370,635, filed on Mar. 7, 2006, now Pat. No. 7,329,534, which is a division of application No. 10/263,975, filed on Oct. 3, 2002, now Pat. No. 7,074,577.

(51) Int. Cl.
*C12M 1/34* (2006.01)

(52) U.S. Cl. ............... 435/287.1; 422/401; 422/405; 435/287.2; 435/288.1; 435/810; 436/518; 436/810

(58) Field of Classification Search ............ None
See application file for complete search history.

(56) References Cited

U.S. PATENT DOCUMENTS

| | | | |
|---|---|---|---|
| 3,786,985 A | 1/1974 | Blaivas | |
| 3,814,248 A | 6/1974 | Lawhead | |
| 3,890,237 A | 6/1975 | Welch | |
| 3,897,340 A | 7/1975 | Ayres | |
| 3,897,343 A | 7/1975 | Ayres | |
| 3,919,085 A | 11/1975 | Ayres | |
| 3,931,018 A | 1/1976 | North, Jr. | |
| 3,957,654 A | 5/1976 | Ayres | |
| 3,970,565 A | 7/1976 | Ahlstrand et al. | |
| 4,027,660 A | 6/1977 | Wardlaw et al. | |
| 4,055,501 A | 10/1977 | Cornell | |
| 4,077,396 A | 3/1978 | Wardlaw et al. | |
| 4,082,085 A | 4/1978 | Wardlaw et al. | |
| 4,083,788 A | 4/1978 | Ferrara | |
| 4,088,582 A | 5/1978 | Murty et al. | |
| 4,091,659 A | 5/1978 | Massey, III et al. | |

(Continued)

*Primary Examiner* — Chris L Chin
(74) *Attorney, Agent, or Firm* — Fay Sharpe LLP; Richard M. Klein

(57) ABSTRACT

A tube and float system for use in separation and axial expansion of the buffy coat is provided. The system includes a transparent, or semi-transparent, flexible sample tube and a rigid separator float having a specific gravity intermediate that of red blood cells and plasma. The sample tube has an elongated sidewall having a first cross-sectional inner diameter. The float consists of a main body portion and one or more support members protruding from the main body portion to engage and support the sidewall of the sample tube. The main body portion and the support members of the float have a cross-sectional diameter less than that of the first cross-sectional inner diameter of the tube when the sample tube is expanded, such as by centrifugation. The main body portion of the float together with an axially aligned portion of the sidewall define an annular volume therebetween. The support members protruding from the main body portion of the float traverse said annular volume to produce one or more analysis areas. During centrifugation, the centrifugal force enlarges the diameter of the tube to permit density-based axial movement of the float in the tube. Thereafter, the centrifugal force is reduced to cause the tube sidewall to return to its first diameter, thereby capturing the float and trapping the buffy coat constituents in the analysis area. The bully coat constituents can then be evaluated or measured.

20 Claims, 8 Drawing Sheets

U.S. PATENT DOCUMENTS

| | | |
|---|---|---|
| 4,116,638 A | 9/1978 | Kenoff |
| 4,135,884 A | 1/1979 | Shen |
| 4,137,755 A | 2/1979 | Wardlaw et al. |
| 4,154,690 A | 5/1979 | Ballies |
| 4,159,896 A | 7/1979 | Levine et al. |
| 4,197,287 A | 4/1980 | Piasio et al. |
| 4,225,575 A | 9/1980 | Piasio et al. |
| 4,294,707 A | 10/1981 | Ikeda et al. |
| 4,305,924 A | 12/1981 | Piasio et al. |
| 4,378,344 A | 3/1983 | Zahradnik et al. |
| 4,417,981 A | 11/1983 | Nugent |
| 4,464,254 A | 8/1984 | Dojki et al. |
| 4,567,754 A | 2/1986 | Wardlaw et al. |
| 4,594,165 A | 6/1986 | Levine et al. |
| 4,717,660 A | 1/1988 | Schulte |
| 4,774,965 A | 10/1988 | Rodriguez et al. |
| 4,823,624 A | 4/1989 | Rodriguez et al. |
| 4,824,560 A | 4/1989 | Alspector |
| 4,877,520 A | 10/1989 | Burns |
| 4,952,054 A | 8/1990 | Levine et al. |
| 4,953,975 A | 9/1990 | Levine et al. |
| 5,086,784 A | 2/1992 | Levine et al. |
| 5,137,832 A | 8/1992 | Levine et al. |
| 5,203,825 A | 4/1993 | Haynes et al. |
| 5,252,460 A | 10/1993 | Fiedler et al. |
| 5,321,975 A | 6/1994 | Levine et al. |
| 5,342,790 A | 8/1994 | Levine et al. |
| 5,354,483 A | 10/1994 | Furse |
| 5,360,719 A | 11/1994 | Levine et al. |
| 5,403,714 A | 4/1995 | Levine et al. |
| 5,494,590 A | 2/1996 | Smith et al. |
| 5,496,704 A | 3/1996 | Fiedler et al. |
| 5,533,518 A | 7/1996 | Vogler |
| 5,547,577 A | 8/1996 | Vogler et al. |
| 5,560,830 A | 10/1996 | Coleman et al. |
| 5,578,446 A | 11/1996 | Harris et al. |
| 5,632,905 A | 5/1997 | Haynes |
| 5,635,362 A | 6/1997 | Levine et al. |
| 5,667,963 A | 9/1997 | Smith et al. |
| 5,736,033 A | 4/1998 | Coleman et al. |
| 5,759,794 A | 6/1998 | Levine et al. |
| 5,776,078 A | 7/1998 | Wardlaw |
| 5,776,710 A | 7/1998 | Levine et al. |
| 5,834,217 A | 11/1998 | Levine et al. |
| 5,851,397 A | 12/1998 | Itoh |
| 5,906,744 A | 5/1999 | Carroll et al. |
| 6,197,523 B1 | 3/2001 | Rimm et al. |
| 6,277,331 B1 | 8/2001 | Konrad |
| 7,074,577 B2 | 7/2006 | Haubert et al. |
| 7,329,534 B2 | 2/2008 | Haubert et al. |
| 7,915,029 B2 | 3/2011 | Haubert et al. |

BUFFY COAT TUBE AND FLOAT SYSTEM AND METHOD

CROSS-REFERENCE TO RELATED APPLICATIONS

This application is a continuation of U.S. patent application Ser. No. 12/029,274, filed Feb. 11, 2008, now U.S. Pat. No. 7,915,029, which was a continuation of U.S. patent application Ser. No. 11/370,635, filed Mar. 7, 2006, now U.S. Pat. No. 7,329,534, which was itself a divisional of U.S. patent application Ser. No. 10/263,975, filed Oct. 3, 2002, now U.S. Pat. No. 7,074,577. These applications are hereby fully incorporated by reference.

FIELD OF THE INVENTION

The present invention relates generally to density-based fluid separation and, in particular, to an improved sample tube and float design for the separation and axial expansion of constituent fluid components layered by centrifugation, and a method employing the same. The present invention finds particular application in blood separation and axial expansion of the buffy coat layers, and will be described with particular reference thereto. However, it will be recognized that the present invention is also amenable to other like applications.

BACKGROUND OF THE INVENTION

Quantitative Buffy Coat (QBC) analysis is routinely performed in clinical laboratories for the evaluation of whole blood. The buffy coat is a series of thin, light-colored layers of white cells that form between the layer of red cells and the plasma when unclotted blood is centrifuged or allowed to stand.

QBC analysis techniques generally employ centrifugation of small capillary tubes containing anticoagulated whole blood, to separate the blood into essentially six layers: (1) packed red cells, (2) reticulocytes, (3) granulocytes, (4) lymphocytes/monocytes, (5) platelets, and (6) plasma. The buffy coat consists of the layers, from top to bottom, of platelets, lymphocytes and granulocytes and reticulocytes.

Based on examination of the capillary tube, the length or height of each layer is determined during the QBC analysis and converted into a cell count, thus allowing quantitative measurement of each layer. The length or height of each layer can be measured with a manual reading device, i.e., a magnification eyepiece and a manual pointing device, or photometrically by an automated optical scanning device that finds the layers by measuring light transmittance and fluorescence along the length of the tube. A series of commonly used QBC instruments are manufactured by Becton-Dickinson and Company of Franklin, Lakes, N.J.

Since the buffy coat layers are very thin, the buffy coat is often expanded in the capillary tube for more accurate visual or optical measurement by placing a plastic cylinder, or float, into the tube. The float has a density less than that of red blood cells (approximately 1.090 g/ml) and greater than that of plasma (approximately 1.028 g/ml) and occupies nearly all of the cross-sectional area of the tube. The volume-occupying float, therefore, generally rests on the packed red blood cell layer and expands the axial length of the buffy coat layers in the tube for easier and more accurate measurement.

There exists a need in the art for an improved sample tube and float system and method for separating blood and/or identifying circulating cancer and/or other rare cells, organisms or particulates or objects (i.e., stem cells, cell fragments, virally-infected cells, trypanosomes, etc.) in the buffy coat or other layers in a blood sample. However, the number of cells expected to be typically present in the buffy coat is very low relative to the volume of blood, for example, in the range of about 1-100 cells per millimeter of blood, thus making the measurement difficult, particularly with the very small sample sizes employed with the conventional QBC capillary tubes and floats.

The present invention contemplates a new and improved blood separation assembly and method that overcome the above-referenced problems and others.

SUMMARY OF THE INVENTION

In a first aspect of the invention, a method of separating and axially expanding the buffy coat constituents in a blood sample includes introducing the blood sample into a flexible sample tube having an elongate sidewall of a first cross-sectional inner diameter. An elongate rigid volume-occupying float is also inserted into, or is present in, the flexible sample tube.

The float has a specific gravity intermediate that of red blood cells and plasma. It includes a main body portion and one or more support members protruding from the main body portion of the float to engage and support the sidewall of the sample tube. The main body portion and the support members have a cross-sectional diameter less than the first inner diameter of the tube when the sample tube is subsequently expanded, such as by centrifugation.

The main body portion of the float, together with an axially aligned portion of the sidewall of the sample tube, defines an annular volume therebetween. The support members protruding from the main body portion of the float traverse the annular volume to engage and support the sidewall of the tube thereby producing one or more analysis areas.

The sample tube containing the blood sample and float is then centrifuged to effect a density-based separation of the blood sample into discrete layers at a rotational speed that causes a resilient expansion or enlargement of the diameter of the sidewall to a second diameter in response to pressure in the blood caused by the centrifugal force, which diameter expansion is sufficiently large to permit axial movement of the float in the tube. During centrifugation, the float is moved into axial alignment with at least the buffy coat layers of the blood sample due to the density of the float. After centrifugation, the rotational speed is reduced and the tube sidewall returns to essentially its first diameter and engages the float. As a result, the buffy coat constituents are trapped in the analysis areas for review, measurement and/or detection by conventional methods.

In a further aspect of the invention, an apparatus for separation and analysis of a target analyte in a sample of anticoagulated whole blood is produced. The apparatus includes a transparent, or semi-transparent, flexible tube for holding the sample, the tube having an elongate sidewall of a first cross-sectional inner diameter. The apparatus further includes an elongate, rigid, volume-occupying float having a specific gravity which is intermediate that of red blood cells and plasma.

The float includes a main body portion having one or more support members protruding from the main body portion. The cross-sectional diameter of the main body portion and/or the support members of the float are less than the first cross-sectional inner diameter of the tube when the sample tube is subsequently expanded. In this regard, the sidewall is resiliently radially expandable to a second diameter in response to pressure or force. The second diameter is sufficiently large to permit axial movement of the float in the tube during centrifugation.

The main body portion of the float, together with an axially aligned portion of the sidewall, defines an annular volume therebetween. The protrusions of the float traverse the annular volume and engage and support the sidewall, forming the analysis area subsequent to centrifugation.

In another aspect, a volume occupying separator float adapted for use with an associated sample tube is provided. The float includes a rigid main body portion and one or more support members protruding from the main body portion of the float to engage and support the sidewall of the sample tube. The main body portion and the support members have a cross-sectional diameter less than an inner diameter of the sample tube when the sample tube is expanded. The main body portion together with an axially aligned portion of the sidewall, define an annular volume therebetween. Additionally, the supporting members protruding from the main body portion of the float traverse the annular volume to engage and support the sidewalls and to produce one or more areas for analysis.

In a still further aspect, a method for detecting circulating target cells, such as epithelial cancer cells, stem cells, cell fragments, virally-infected cells, trypanosomes, etc., in an anticoagulated whole blood sample is provided. This method includes combining the blood sample with one or more target cell epitope-specific-labeling agents so as to differentiate the target cells from other cells in the blood sample. The blood sample and a volume-occupying separator float are placed into a transparent, or semi-transparent, flexible sample tube. The separator float has a specifically defined specific gravity. It comprises a rigid main body portion and tube support members. The separator float in conjunction with the sidewalls produces one or more areas of analysis. Additionally, the float has a cross-sectional diameter less than an inner diameter of the sample tube when the sample tube is expanded. The blood sample and separator float are centrifuged in the sample tube to effect centrifugally motivated localization of any target cells present in the blood sample to the areas of analysis. The blood sample present in the analysis areas is then examined to identify whether any target cells are present.

One advantage of the present invention is found in a blood separating apparatus that can separate the entire buffy coat of a relatively large blood sample from the rest of the blood volume.

Another advantage of the invention resides in the fact that the buffy coat layers can be made available for visualization or imaging in one simple operation, i.e., the application of pressure and/or centrifugation.

Still another advantage of the invention resides in enhanced buffy coat separation, retention, and, if desired, removal from the sample tube for further processing.

Yet another advantage of the invention is found in that the tolerance precision between the float and tube is decreased over that necessary for the prior art QBC-type systems, thus reducing the necessary cost of the components.

Still another advantage is found in that the tube can be supported for improved imaging of the sample, and a more repeatable depth for imaging may be provided.

Still further advantages of the present invention reside in its relatively simple construction, ease of manufacture, and low cost.

In a still additional aspect, the compressibility and/or rigidity of the flexible tube and rigid float can be reversed. In this aspect, the float is designed to shrink in diameter at the higher pressures and moves freely within a rigid, or optionally, semi-rigid tube. The use of a compressible float allows for usage of transparent glass tubes which, in some instances, exhibit enhanced optical properties over polymeric tubes. Furthermore, this aspect generally reduces the tolerance requirements for the glass tubes (since the float would expand up against the tube wall after the pressure decreases), and a full range of float designs is possible.

In another aspect, the step of centrifugation is not required. In such an aspect, the application of pressure alone to the inside of the tube, or simply the expansion of the tube (or the compression of the float), is required. For example, such pressure can be produced through the use of a vacuum source on the outside of the tube. Such an application also allows for the top of the sample tube to be kept open and easily accessible. Additionally, the use of a vacuum source may be easier to implement in some situations than the application of a centrifugal force.

Additionally, any method of tubular expansion/contraction (or float compression) such as mechanical, electrical, magnetic, etc., can be implemented. Once the tube is expanded (or the float is compressed), the float will move to the proper location due to buoyancy forces created by the density variations within the sample.

In a further aspect, the float comprises a part of a collection tube system or assembly. In this aspect, it is not necessary to transfer the sample from a collection container to an analysis tube. The blood or sample fluid can be collected immediately and then tested. Such a system is somewhat faster, and also safer from a biohazard standpoint. For example, this system is desirable in very contagious situations (i.e. Ebola virus, HIV, etc.) where any type of exposure of the blood must be minimized.

Still further advantages and benefits of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings, in which like reference numerals denote like components throughout the several views, are only for purposes of illustrating various embodiments of the invention and are not to be construed as limiting the invention.

DETAILED DESCRIPTION OF THE PREFERRED EMBODIMENTS

Figure 1:
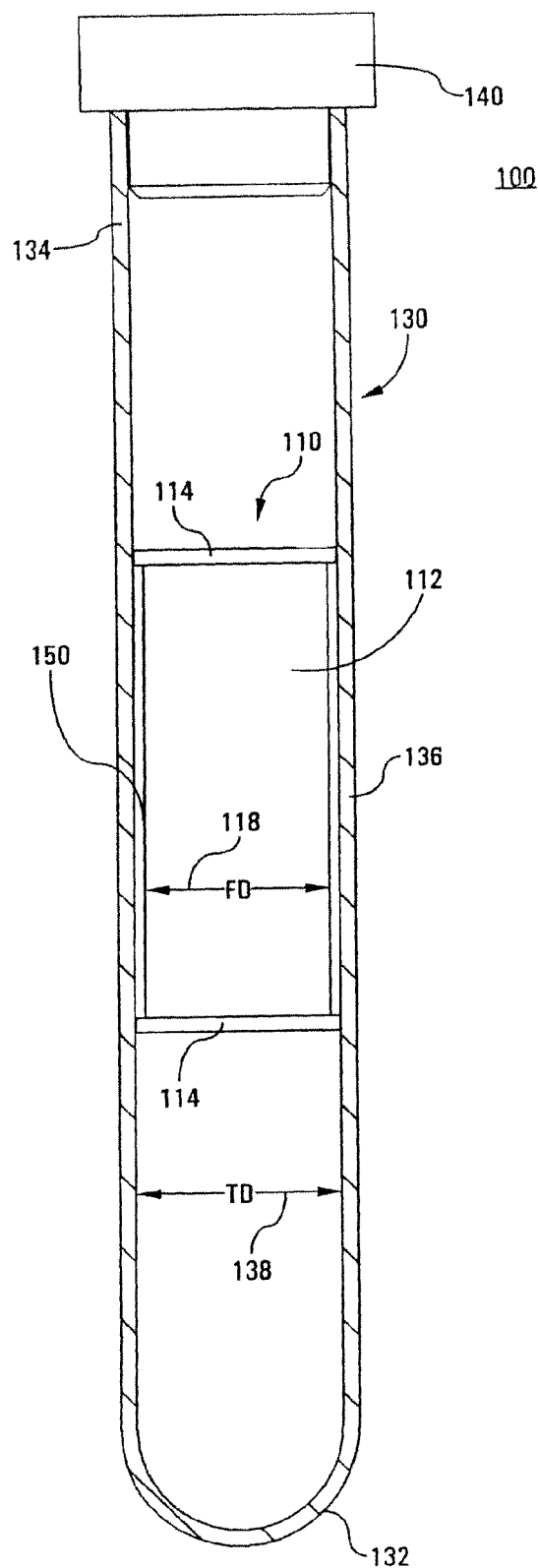
FIG. 1 is a sectional view of a sample tube containing a generally spool-shaped separator float according to an exemplary embodiment of the invention.

Turning now to the drawings, wherein the showings are for purposes of illustrating the preferred embodiments of the invention only and not for limiting the same, FIG. 1 shows a blood separation tube and float assembly 100, including a sample tube 130 having a separator float or bobber 110 of the invention therein.

The sample tube 130 is generally cylindrical in the depicted embodiment, although tubes having polygonal and other geometrical cross-sectional shapes are also contemplated. The sample tube 130 includes a first, closed end 132 and a second, open end 134 receiving a stopper or cap 140. Other closure means are also contemplated, such as parafilm or the like. In alternative embodiments, not shown, the sample tube may be open at each end, with each end receiving an appropriate closure device.

Although the tube is depicted as generally cylindrical, the tube 130 may be minimally tapered, slightly enlarging toward the open end 134, particularly when manufactured by an injection molding process. This taper or draft angle is generally necessary for ease of removal of the tube from the injection molding tool.

The tube 130 is formed of a transparent or semi-transparent material and the sidewall 136 of the tube 130 is sufficiently flexible or deformable such that it expands in the radial direction during centrifugation, e.g., due to the resultant hydrostatic pressure of the sample under centrifugal load. As the centrifugal force is removed, the tube sidewall 136 substantially returns to its original size and shape.

The tube may be formed of any transparent or semi-transparent, flexible material (organic and inorganic), such as polystyrene, polycarbonate, styrene-butadiene-styrene ("BBB"), styrene/butadiene copolymer (such as "K-Resin®" available from Phillips 66 Co., Bartlesville, Okla.), etc. Preferably, the tube material is transparent. However, the tube does not necessarily have to be clear, as long as the receiving instrument that is looking for the cells or items of interest in the sample specimen can "see" or detect those items in the tube. For example, items of very low level of radioactivity that can't be detected in a bulk sample can be detected through a non-clear or semi-transparent wall after it is separated by the process of the present invention and trapped near the wall by the float 110 as described in more detail below.

In a preferred embodiment, the tube 130 is sized to accommodate the float 110 plus at least about five milliliters of blood or sample fluid, more preferably at least about eight milliliters of blood or fluid, and most preferably at least about ten milliliters of blood or fluid. In an especially preferred embodiment, the tube 130 has an inner diameter 138 of about 1.5 cm and accommodates at least about ten milliliters of blood in addition to the float 110.

The float 110 includes a main body portion 112 and two sealing rings or flanges 114, disposed at opposite axial ends of the float 110. The float 110 is formed of one or more generally rigid organic or inorganic materials, preferably a rigid plastic material, such as polystyrene, acrylonitrile butadiene styrene (ABS) copolymers, aromatic polycarbonates, aromatic polyesters, carboxymethylcellulose, ethyl cellulose, ethylene vinyl acetate copolymers, nylon, polyacetals, polyacetates, polyacrylonitrile and other nitrile resins, polyacrylonitrile-vinyl chloride copolymer, polyamides, aromatic polyamides (aramids), polyamide-imide, polyarylates, polyarylene oxides, polyarylene sulfides, polyarylsulfones, polybenzimidazole, polybutylene terephthalate, polycarbonates, polyester, polyester imides, polyether sulfones, polyetherimides, polyetherketones, polyetheretherketones, polyethylene terephthalate, polyimides, polymethacrylate, polyolefins (e.g., polyethylene, polypropylene), polyallomers, polyoxadiazole, polyparaxylene, polyphenylene oxides (PPO), modified PPOs, polystyrene, polysulfone, fluorine containing polymer such as polytetrafluoroethylene, polyurethane, polyvinyl acetate, polyvinyl alcohol, polyvinyl halides such as polyvinyl chloride, polyvinyl chloride-vinyl acetate copolymer, polyvinyl pyrrolidone, polyvinylidene chloride, specialty polymers, and so forth, and most preferably polystyrene, polycarbonate, polypropylene, acrylonitrite butadiene-styrene copolymer ("ABS") and others.

In this regard, one of the objectives of the present invention is to avoid the use of materials and/or additives that interfere with the detection or scanning method. For example, if fluorescence is utilized for detection purposes, the material utilized to construct the float 110 must not have interfering or "background" fluorescence at the wavelength of interest.

The main body portion 112 and the sealing rings or support members 114 of the float 110 are sized to have an outer diameter 118 which is less than the inner diameter 138 of the sample tube 130, under pressure or centrifugation. The main body portion 112 of the float 110 is also less than the sealing or support rings 114, thereby defining an annular channel 150 between the float 110 and the sidewall 136 of the tube 130. The main body portion occupies much of the cross-sectional area of the tube, the annular gap 150 being large enough to contain the cellular components of the buffy coat layers and associated target cells when the tube is the non-flexed state. Preferably, the dimensions 118 and 138 are such that the annular gap 150 has a radial thickness ranging from about 25-250 microns, most preferably about 50 microns.

While in some instances the outer diameter 118 of the main body portion 112 of the float 110 may be less than the inner diameter 138 of the tube 130, this relationship is not required. This is because once the tube 130 is centrifuged (or pressurized), the tube 130 expands and the float 110 moves freely. Once the centrifugation (or pressurization) step is completed, the tube 130 constricts back down on the sealing rings or support ridges 114. The annular gap or channel 150 is then created, and sized by the height of the support ridges or sealing rings 114 (i.e., the depth of the "pool" is equal to the height of the support ridges 114, independent of what the tube diameter is/was).

In an especially preferred embodiment, the float dimensions are 3.5 cm tall×1.5 cm in diameter, with a main body portion sized to provide a 50-micron gap for capturing the buffy coat layers of the blood. Thus, the volume available for the capture of the buffy coat layer is approximately 0.08 milliliter. Since the entire buffy coat layer is generally less than about 0.5% of the total blood sample, the preferred float accommodates the entire quantity of buffy layer separated in an eight to ten milliliter sample of blood.

The sealing or support flanged ends 114 are sized to be roughly equal to, or slightly greater than, the inner diameter 138 of the tube. The float 110, being generally rigid, can also provide support to the flexible tube wall 136. Furthermore, the large diameter portions 114 provide a sealing function to maintain separation of the blood constituent layers. The seal formed between the large diameter regions 114 of the float and the wall 136 of the tube may form a fluid-tight seal. As used herein, the term "seal" is also intended to encompass near-zero clearance or slight interference between the flanges 114 and the tube wall 136 providing a substantial seal which is in most cases, adequate for purposes of the invention.

The sealing rings 114 are most preferably continuous ridges, in which case the sample may be centrifuged at lower speeds and slumping of the separated layers is inhibited. However, in alternative embodiments, the sealing ridges can be discontinuous or segmented bands having one or openings providing a fluid path in and out of the annular gap 150. The sealing ridges 114 may be separately formed and attached to the main body portion 112. Preferably, however, the sealing ridges 114 and the main body portion 112 form a unitary or integral structure.

The overall specific gravity of the separator float 110 should be between that of red blood cells (approximately 1.090) and that of plasma (approximately 1.028). In a preferred embodiment, the specific gravity is in the range of from about 1.089-1.029, more preferably from about 1.070 to about 1.040, and most preferably about 1.05.

The float may be formed of multiple materials having different specific gravities, so long as the overall specific gravity of the float is within the desired range. The overall specific gravity of the float 110 and the volume of the annular gap 150 may be selected so that some red cells and/or plasma may be retained within the annular gap, as well as the buffy coat layers. Upon centrifuging, the float 110 occupies the same axial position as the buffy coat layers and target cells and floats on the packed red cell layer. The buffy coat is retained in the narrow annular gap 150 between the float 110 and the inner wall 136 of the tube 130. The expanded buffy coat region can then be examined, under illumination and magnification, to identify circulating epithelial cancer or tumor cells or other target analytes.

In one preferred embodiment, the density of the float 110 is selected to settle in the granulocyte layer of the blood sample.

The granulocytes settle on, or just above, the packed red-cell layer and have a specific gravity of about 1.08-1.09. In this preferred embodiment, the specific gravity of the float is in this range of from about 1.08 to about 1.09 such that, upon centrifugation, the float settles in the granulocyte layer. The amount of granulocytes can vary from patient to patient by as much as a factor of about twenty. Therefore, selecting the float density such that the float settles in the granulocyte layer is especially advantageous since loss of any of the lymphocyte/monocyte layer, which settles just above the granulocyte layer, is avoided. During centrifugation, as the granulocyte layer increases in size, the float settles higher in the granulocytes and keeps the lymphocytes and monocytes at essentially the same position with respect to the float.

The method for detecting circulating epithelial cancer cells in a blood of a subject is disclosed in U.S. Pat. No. 6,197,523 may advantageously be modified to employ the sample tube and float system of the subject invention. The aforementioned U.S. Pat. No. 6,197,523 is incorporated herein by reference in its entirety.

In a preferred exemplary method of using the tube/float system 100 of the invention, a sample of anticoagulated blood is provided. For example, the blood to be analyzed may be drawn using a standard Vacutainer® or other like blood collection device of a type having an anticoagulant predisposed therein.

A fluorescently labeled antibody, which is specific to the target epithelial cells or other target analytes of interest, can be added to the blood sample and incubated. In an exemplary embodiment, the epithelial cells are labeled with anti-epcam having a fluorescent tag attached to it. Anti-epcam binds to an epithelial cell-specific site that is not expected to be present in any other cell normally found in the blood stream. A stain or colorant, such as acridine orange, may also be added to the sample to cause the various cell types to assume differential coloration for ease of discerning the buffy coat layers under illumination and to highlight or clarify the morphology of epithelial cells during examination of the sample.

The blood is then transferred to the assembly 100 for centrifugation. The float 110 may be fitted into the tube 130 after the blood sample is introduced into the sample tube 130 or otherwise may be placed therein beforehand. The tube and float assembly 100 containing the sample is then centrifuged. Operations required for centrifuging the blood by means of the subject tube/float system 100 are not expressly different from the conventional case, although, as stated above, reduced centrifuge speeds may be possible and problems of slumping may be reduced. An adaptor may optionally be utilized in the rotor to prevent failure of the flexible tube due to stress.

When the centrifugation is started, the resultant hydrostatic pressure deforms or flexes the wall 136 so as to enlarge the diameter of the tube. The blood components and the float 110 are thus free to move under centrifugal force within the tube 130. The blood sample is separated into six distinct layers according to density, which are, from bottom to top: packed red blood cells, reticulocytes, granulocytes, lymphocytes/monocytes, platelets, and plasma. The epithelial cells sought to be imaged tend to collect by density in the buffy coat layers, i.e., in the granulocyte, lymphocyte/monocyte, and platelet layers. Due to the density of the float, it occupies the same axial position as the buffy coat layers which thus occupy the narrow annular gap 150, potentially along with a small amount of the red cell and/or plasma).

After centrifugal separation is complete and the centrifugal force is removed, the tube 130 returns to its original diameter to capture or retain the buffy coat layers and target analytes within the annular gap 150. The tube/float system 100 is transferred to a microscope or optical reader to identify any target analytes in the blood sample.

Figure 2:
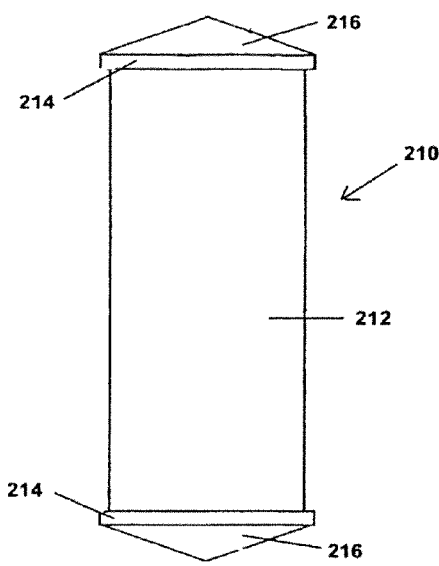
FIG. 2 is an elevational view of a separator float having generally conical ends according to another exemplary embodiment of the invention.

FIGS. 2-28 illustrate several exemplary modifications of the float according to the invention. FIG. 2 illustrates a float 210 that is similar to the float 110 shown and described by way of reference to the of FIG. 1, which includes a main body portion 212 and sealing rings 214, but which further including a tapered or cone-shaped endcap member 216 disposed at each end. The tapered endcaps 216 are provided to facilitate and direct the flow of cells past the float 210 and sealing ridges 214 during centrifugation.

Figure 3:
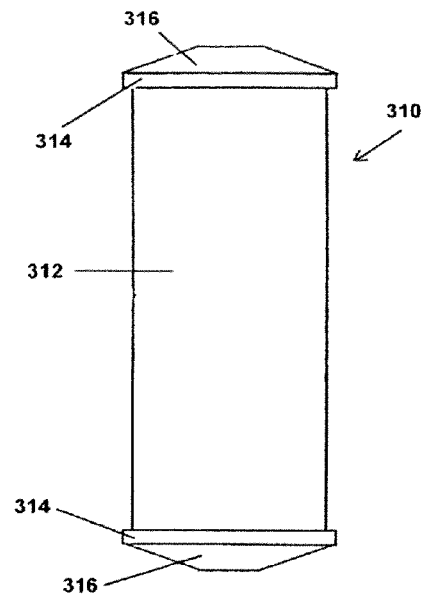
FIG. 3 is an elevational view of a separator float having generally frustoconical ends according to another exemplary embodiment of the invention.

FIG. 3 illustrates a float 310, which is similar to the float 210 shown and described by way of reference to FIG. 2, including a main body portion 312 and sealing ridges 314, but having truncated cone-shaped endcap members 316, disposed at each end. The frustoconical endcaps 316 are provided to facilitate the movement or flow of cells and the float during centrifugation.

Figure 4:
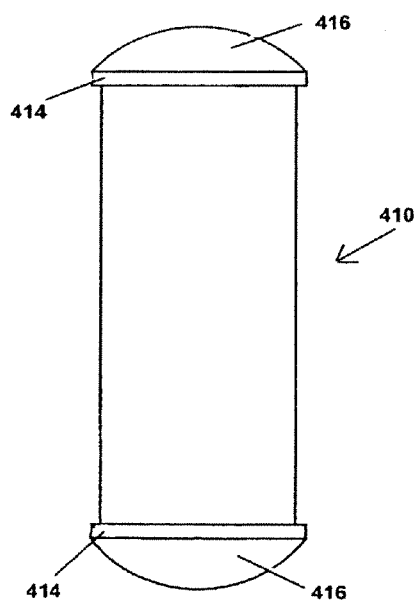
FIG. 4 is an elevational view of a separator float according to yet another exemplary embodiment, wherein the ends are generally convex or dome shaped.

FIG. 4 illustrates a float 410, which is substantially as shown and described by way of reference to the floats 210 and 310 of FIGS. 2 and 3, respectively, but where instead, generally convex or dome-shaped members 416, which cap the sealing ridges 414. The endcaps 416 may be hemispherical, hemiellipsoidal, or otherwise similarly sloped, are provided. Again, the sloping ends 416 are provided to facilitate density-motivated cell and float movement during centrifugation.

The geometrical configurations of the endcap units 216, 316, and 416 illustrated in FIGS. 2-4, respectively, are intended to be exemplary and illustrative only, and many other geometrical shapes (including concave or convex configurations) providing a curved, sloping, and/or tapered surface around which the blood sample may flow during centrifugation. Additional exemplary shapes contemplated include, but are not limited to tectiform and truncated tectiform; three, four, or more sided pyramidal and truncated pyramidal, ogival or truncated ogival; geodesic shapes, and the like.

Figure 5:
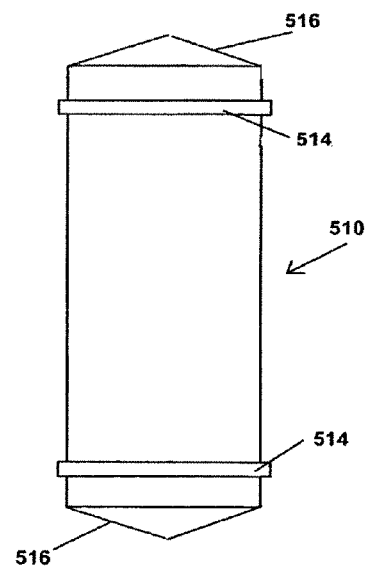
FIG. 5 is an elevational view of a separator float according to still another exemplary embodiment having sealing ridges offset from the ends.

FIG. 5 illustrates a float 510 similar to the embodiment depicted in FIG. 1, but wherein the sealing ridges are 514 are axially displaced from the ends. Optional endcap members 516 appear as conical in the illustrated embodiment. However, it will be recognized that the endcaps 516, if present, any other geometrical configuration which provides a sloped or tapered surface may be used, as described above.

Although the remaining FIGS. 6-28 are illustrated with generally flat ends, i.e., without tapered ends, it will be recognized that each of the illustrated embodiments may optionally be modified to include any of the end cap types shown above in FIGS. 2-5, or other geometrical configuration which provide a sloped or tapered surface.

Figure 6:
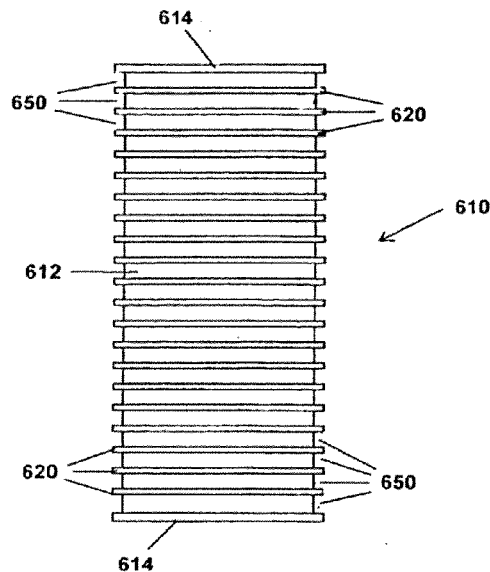
FIGS. 6-8 are elevational views of ribbed separator floats according to further exemplary embodiments of the invention.

FIGS. 6-13 illustrate embodiments of the invention having generally annular tube support members. FIG. 6 illustrates a ribbed float 610 having a plurality of annular ribs or ridges 620 axially spaced along a central body portion 612. Optional end sealing ridges 614 are disposed at opposite ends of the float. The ribs 620 and the optional end sealing ridges 614 are sized to provide a sealing engagement with the tube 130 (FIG. 1) when a centrifugal force is removed. The flexible tube expands during centrifugation to permit flow therearound during the density-based centrifugal separation process. The main body portion 612 has a diameter smaller than the inner diameter of the tube during centrifugation and while supported by rib 614 and, thus, multiple annular channels 650 are defined between the main body portion 612 and the inner tube wall upon completion of the centrifugation process.

Although the illustrated embodiment in FIG. 6 depicts continuous ribs, it will be recognized that the support ribs may likewise be broken or segmented to provide an enhanced flow path between adjacent annular channels 650. Additionally, multiple ribs and/or sealing ridges may be present in order to provide support for the deformable tube and/or to prevent the tube walls from collapsing inwardly.

Figure 7:
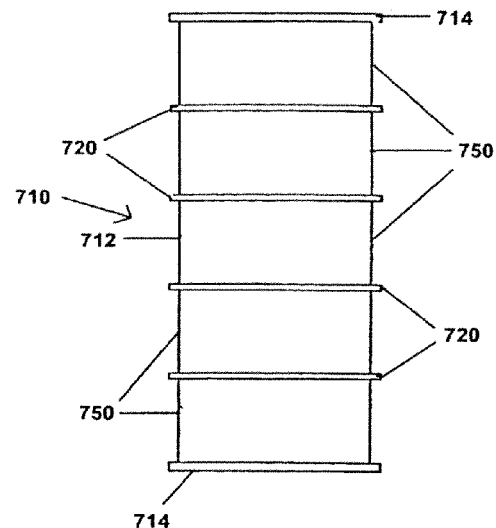

FIG. 7 illustrates a float 710 according to a further embodiment. The float 710 is similar to the float 610 shown in FIG. 6, and has a plurality of ribs 720 axially spaced along a central body portion 712, and wherein plural annular channels 750 are defined therebetween as described above, but wherein the tube support ribs 720 are less densely spaced apart than in the FIG. 6 embodiment. Optional sealing ridges 714 are disposed at opposite ends of the float. Again, the illustrated embodiment depicts continuous ribs, however, it will be recognized that the support ribs may likewise be broken or segmented to provide an enhanced flow path between adjacent annular channels 750.

Figure 8:
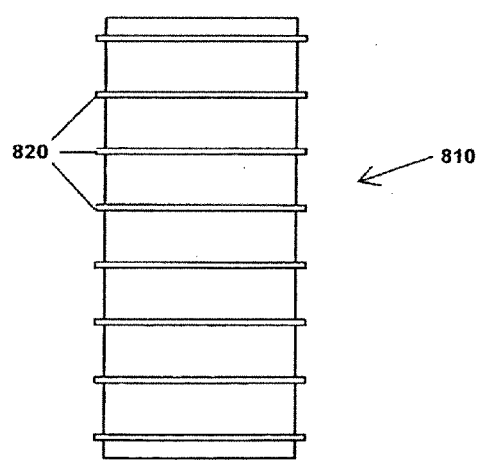

FIG. 8 illustrates a further float embodiment 810, similar to the embodiments of FIGS. 6 and 7, the above descriptions of which are equally applicable thereto. However, the float 810 differs in that it lacks sealing ridges at the opposite ends thereof, which may optionally be provided, and the spacing of the ribs 820 is intermediate the rib spacing shown in FIGS. 6 and 7.

Figure 9:
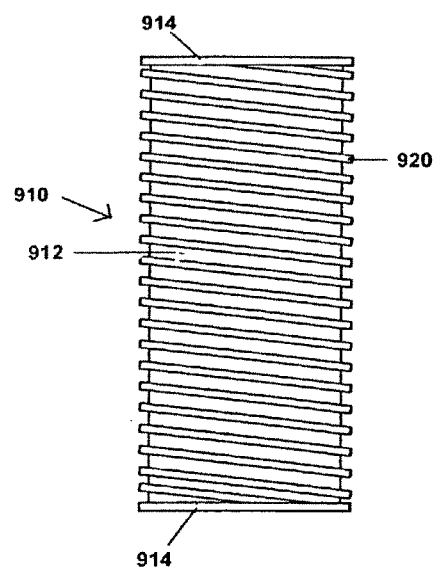
FIG. 9 is an elevational view of a separator float according to another exemplary embodiment of the present invention having generally helical tube support ridges.

FIG. 9 illustrates a further float embodiment 910, wherein a helical support member or ridge 920 is provided. That is, instead of discrete annular bands, multiple turns of the helical ridge 920 provides a series of spaced apart ridges on the main body portion 912, which defines a corresponding helical channel 950. The helical ridge 920 is illustrated as continuous, however, the helical band may instead be segmented or broken into two or more segments, e.g., to provide path for fluid flow between adjacent turns of the helical buffy coat retention channel 950. Optional sealing ridges 914 appear at each axial end of the float 910.

Figure 10:
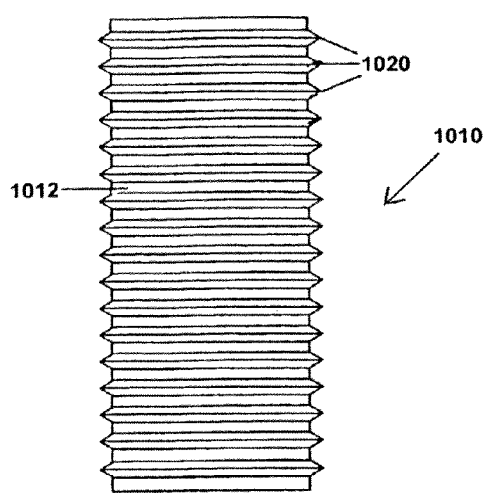
FIG. 10 is an elevational view of a separator float according to a further embodiment of the invention having support ribs, which are tapered in the radial direction.
Figure 11:
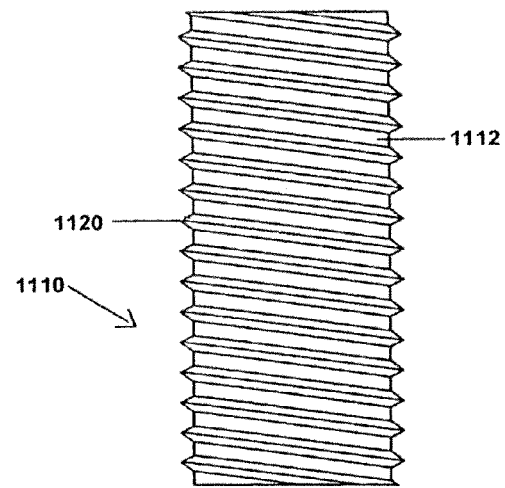
FIG. 11 is an elevational view of a separator float according to yet another exemplary embodiment of the present invention having generally tapered, helical tube support ridges.

FIGS. 10 and 11 illustrate further ribbed and helical float embodiments 1010 and 1110, respectively. In FIG. 10, annular support ribs 1020, on a main body portion 1012, are tapered in the radial dimension. In FIG. 11, a tapered helical support 1120 appears, formed on a main body portion 1112. The floats 1010 and 1110 are otherwise as described above by way of reference to FIGS. 6 and 9, respectively. Although the support members 1020 and 1120 are shown as continuous, they may alternatively be discontinuous or segmented to facilitate axial flow. Option sealing ridges, as described above, at opposite axial ends of the floats 1010 and 1110 are omitted in the illustrated embodiment, and may optionally be provided.

Figure 12:
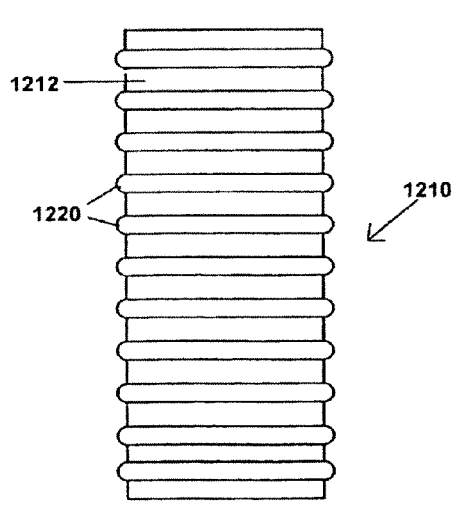
FIG. 12 is an elevational view of a separator float according to another embodiment of the invention having support ribs, which are rounded in cross-sectional shape.
Figure 13:
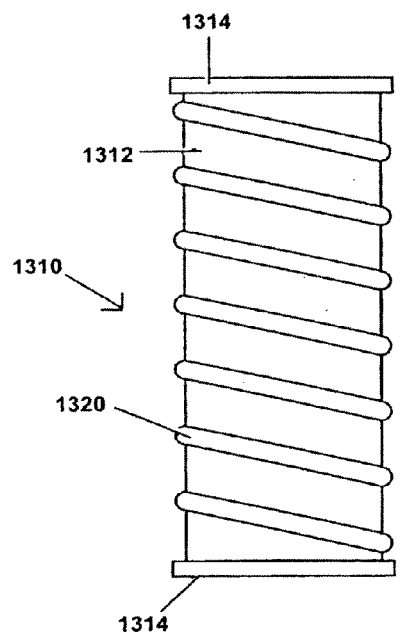
FIG. 13 is an elevational view of a separator float according to another embodiment of the invention having helical support ridges, which are rounded in cross-sectional shape.

FIGS. 12 and 13 illustrate still further ribbed and helical float embodiments 1210 and 1310, respectively. Appearing are support members 1220 and 1320, formed on respective main body portions 1212 and 1312. The tube support members 1220 and 1320 each have a generally curved or rounded cross-sectional profile. The floats 1210 and 1310 are otherwise as described above by way of reference to FIGS. 6 and 9, respectively. Again, the support members 1220 and 1320 are shown as continuous but may, in alternative embodiments, be discontinuous or segmented. Optional end sealing ridges 1314 appear in FIG. 13. Furthermore, end sealing ridges do not appear in FIG. 12, but may optionally be provided.

Figure 14:
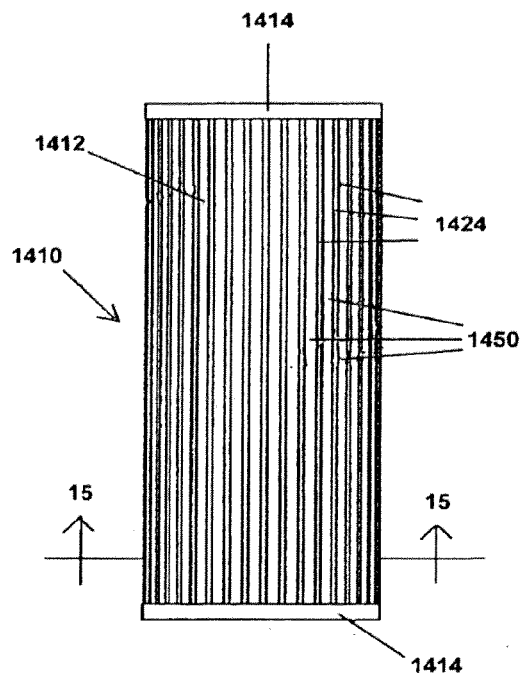
FIG. 14 is an elevational view of a splined separator float according to another exemplary embodiment of the invention.
Figure 15:
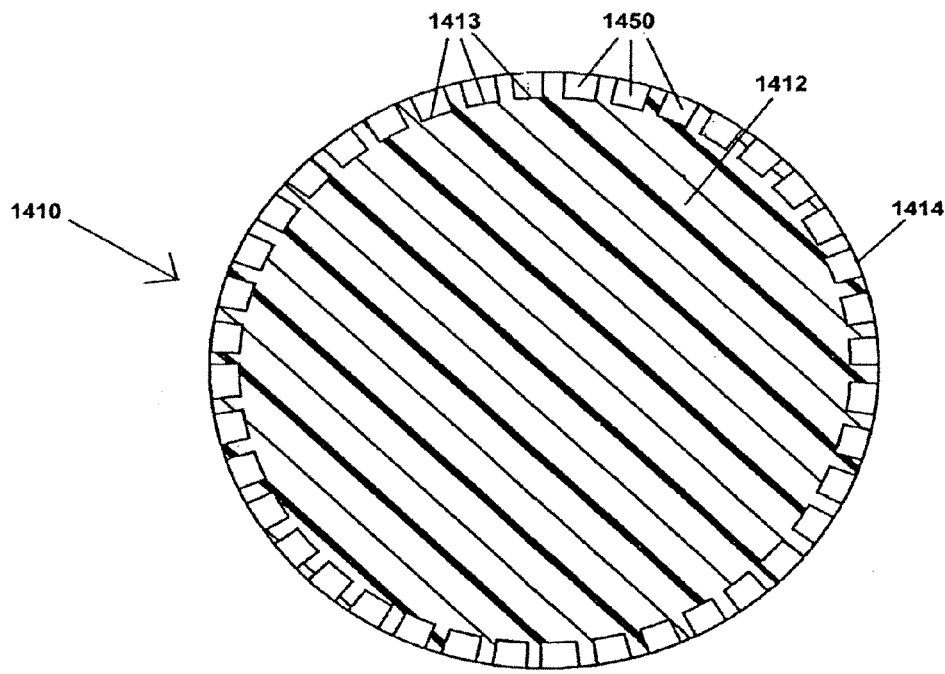
FIG. 15 is an enlarged cross-sectional view taken along the lines 15-15 shown in FIG. 14.

Referring now to FIGS. 14 and 15, there is shown a splined separator float 1410. The float 1410 includes a plurality of axially-oriented splines or ridges 1424 radially spaced about a central body portion 1412. Optional end sealing ridges 1414 are disposed at opposite ends of the float. The splines 1424 and the optional end sealing ridges 1414 protrude from the main body 1412 to engage and provide support for the deformable tube. Where provided, the end sealing ridges 1414 provide a sealing function as described above. The axial protrusions 1424 define fluid retention channels 1450, between the tube inner wall and the main body portion 1412. The surfaces 1413 of the main body portion disposed between the protrusions 1424 may be curved, e.g., when the main body portion is cylindrical, however, flat surfaces 1413 are also contemplated. Although the illustrated embodiment depicts splines 1424 that are continuous along the entire axial length of the float, segmented or discontinuous splines are also contemplated.

Figure 16:
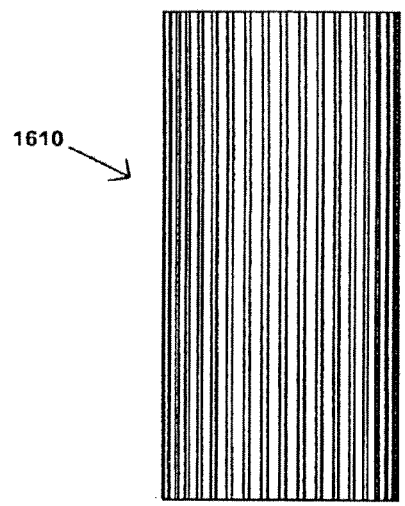
FIG. 16 is an elevational view of a further splined separator float embodiment of the invention.

FIG. 16 illustrates a further splined float embodiment 1610 similar to the float 1410 as shown and described above by way of reference to FIGS. 14 and 15, but wherein optional end sealing ridges are not provided.

Figure 17:
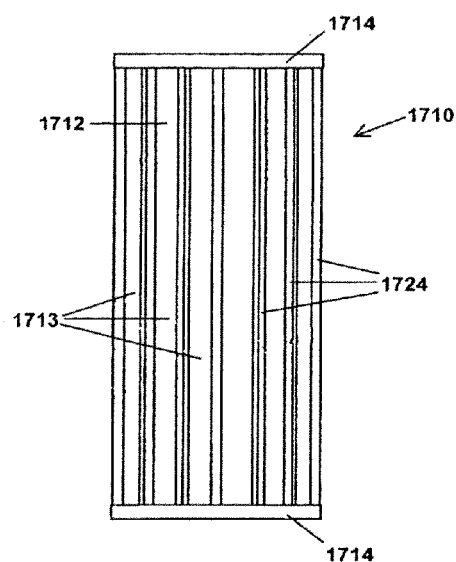
FIGS. 17 and 18 are elevational views of additional splined float embodiments in accordance the invention.
Figure 18:
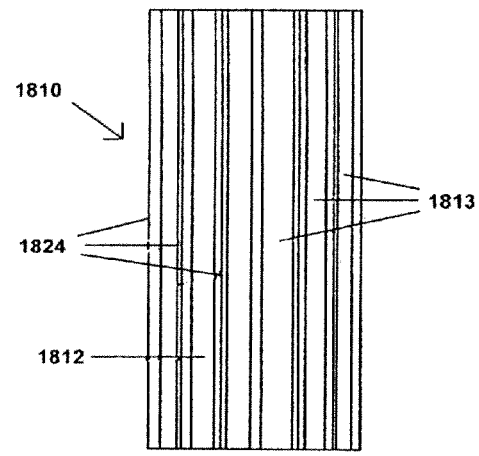

FIGS. 17 and 18 are elevational views of alternative splined floats 1710 and 1810, respectively, and are similar to the respective embodiments shown and described above by way of reference to respective FIGS. 14 and 16, but wherein the axial splines 1724 and 1824, respectively, protruding from respective main body portions 1712 and 1812 are more sparsely radially spaced. The float 1710 includes optional end sealing ridges 1714; such do not appear on the float 1810 of FIG. 18. As above, the respective surfaces 1713 and 1813 may be flat or curved.

Figure 19:
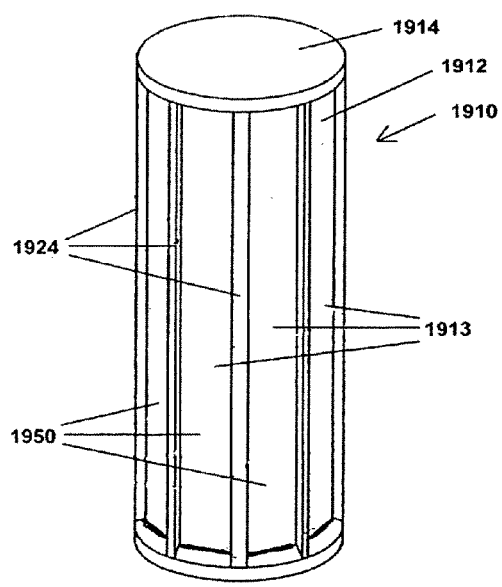
FIG. 19 is a perspective view of yet another splined float embodiment of the present invention.

Referring now to FIG. 19, there is shown a perspective view of a splined separator float 1910 in accordance with a further embodiment of the invention. Multiple axially oriented splines 1924 are spaced radially about and protrude from a central body portion 1912 to provide support for the flexible tube. Optional sealing end ridges 1914 are disposed at opposite ends of the float 1910. Fluid retention channels 1950 formed between adjacent splines 1924 are defined by adjacent splines 1924 and surfaces 1913 on the main body portion 1912. The surfaces 1913 are depicted as generally flat, although curved surfaces are also contemplated. The axial splines 1924 are depicted as continuous along the length of the tube; however, segmented or discontinuous splines are also contemplated.

Figure 20:
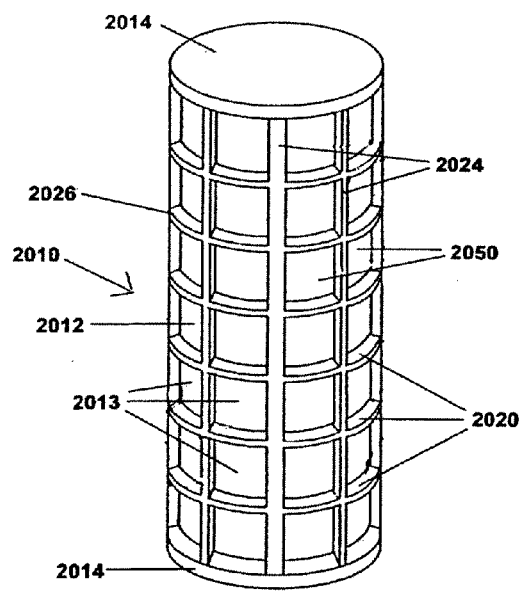
FIG. 20 is a perspective view of a float of still another exemplary embodiment wherein the support ridges include intersecting annular ribs and splines.

Referring now to FIG. 20, there is shown yet another embodiment 2010, including a tube supporting member 2026 protruding with respect to a main body portion 2012. The support means 2026 can be described as an intersecting network of annular rings or ribs 2020 and axial splines 2024. Optional end sealing ridges 2014 are disposed at opposite ends of the float. The support member 2026 and the optional sealing ridges 2014 radially protrude from the main body portion 2012 at opposite ends of the float to engage and provide support for the deformable tube. Where provided, the end sealing ridges 2014 provide a sealing function as described above. The raised support member 2026 defines a plurality of fluid retention windows 2050 formed between the tube inner wall and the main body portion 2012. Surfaces 2013 of the main body portion 2012 corresponding to the windows 2050 may be curved, e.g., when the main body portion is cylindrical, however, flat surfaces 2013 are also contemplated. Although the illustrated embodiment depicts the support member 2026 as a network of annular ribs and axial splines which is continuous, breaks may also be includes in the annular and/or axial portions of the network 2026, e.g., to provide a fluid path between two or more of the windows 2050.

Figure 21:
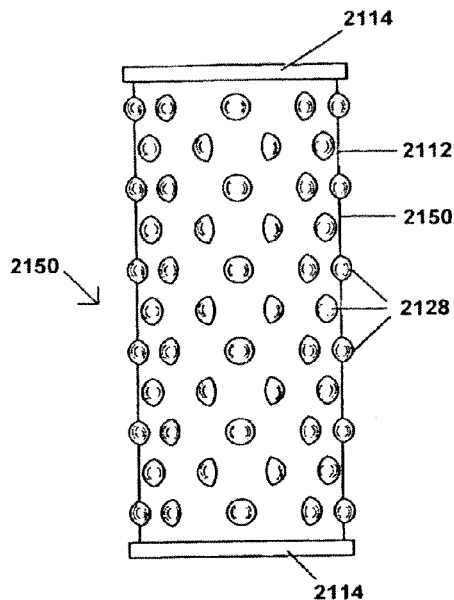
FIGS. 21-26 are elevational views of knobbed or studded separator floats having generally rounded protrusions in various configurations, in accordance with further exemplary embodiments of the present invention.
Figure 22:
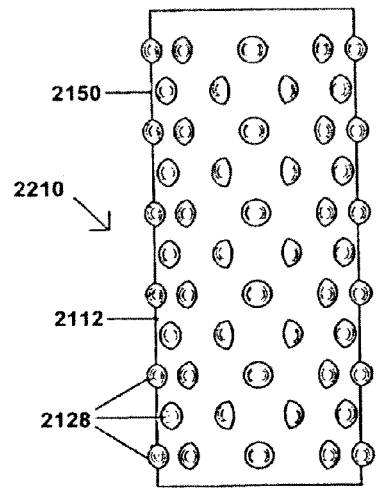

FIGS. 21-26 illustrate several floats having a plurality of protrusions thereon for providing support for the deformable walls of the sample tube. Referring to FIGS. 21 and 22, float 2110 and 2210, respectively, include multiple rounded bumps or knobs 2128 spaced over the surface of a central body portion 2112. Optional end sealing ridges 2114 (FIG. 21) are disposed at opposite ends of the float 2110 and do not appear on the float 2210 of FIG. 22. The knobs 2128 and the optional end sealing ridges 2114 radially protrude from the main body 2112 and traverse an annular gap 2150 to engage and provide support for the deformable tube wall. Where provided, the end sealing ridges 2114 provide a sealing function as described above. The surface of the main body portion disposed between the protrusions may be curved, e.g., when the main body portion is cylindrical, or, alternatively, may have flat portions or facets.

Figure 23:
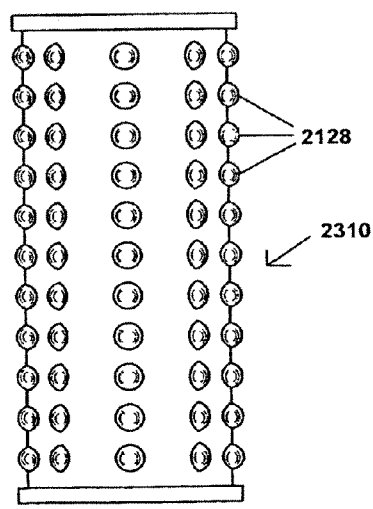
Figure 24:
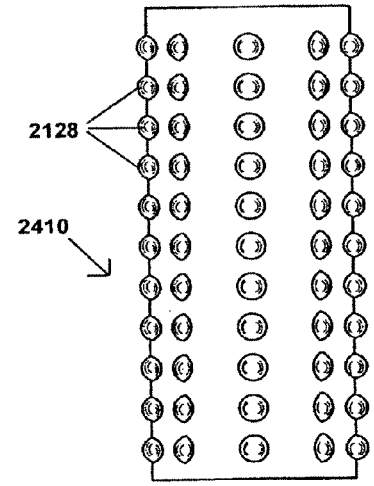

In FIGS. 23 and 24, there are illustrated float embodiments 2310 and 2410, which are as substantially as described above by way of reference to FIGS. 21 and 22, respectfully, but wherein the protrusions 2328 form an aligned rather than staggered pattern over the surface of the main body portion 2312. Optional end sealing ridges 2314 appear in the FIG. 23 embodiment.

Figure 25:
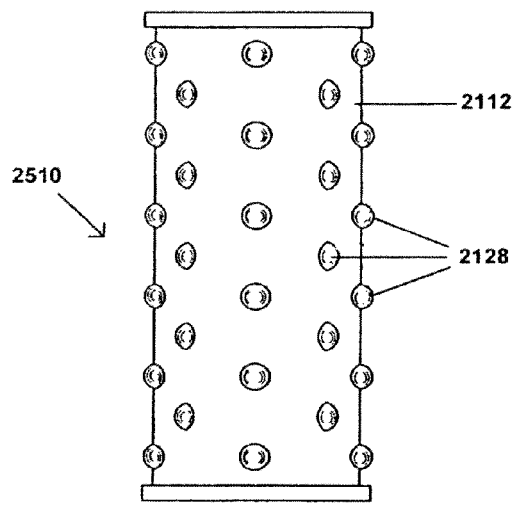
Figure 26:
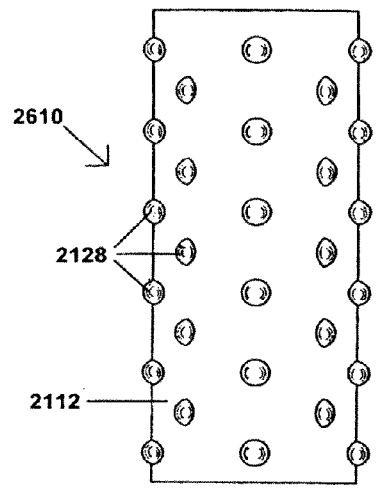

Referring now to FIGS. 25 and 26, there are illustrated float embodiments 2510 and 2610, which are as substantially as described above by way of reference to FIGS. 21 and 22, respectfully, but wherein the protrusions 2528 are less densely spaced over the surface of the main body portion 2512. Optional end sealing ridges 2514 appear in the FIG. 25 embodiment.

Figure 27:
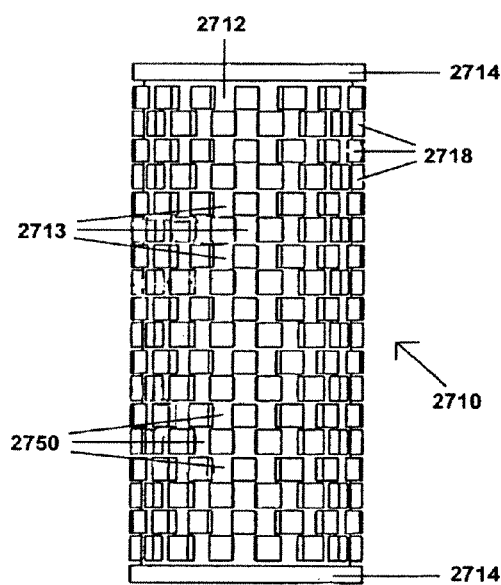
FIGS. 27 and 28 are elevational views of spiked or studded separator floats having facet-like protrusions according to additional exemplary embodiments of the invention.
Figure 28:
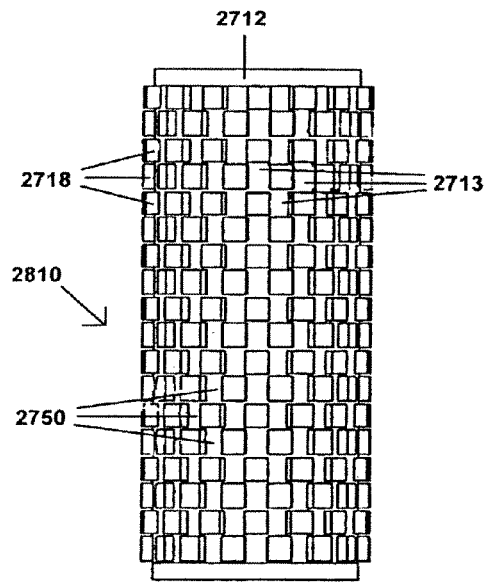

FIGS. 27 and 28 illustrate float embodiments 2710 and 2810, respectively, which include multiple raised facets 2728 spaced over the surface of a central body portion 2712. Optional end sealing ridges 2714 (FIG. 27) are disposed at opposite ends of the float 2710, and do not appear in the FIG. 28 embodiment. The facets 2728 and the optional end sealing ridges 2714 radially protrude from the main body 2712 and traverse an annular gap to engage and provide support for the deformable tube wall and define a plurality of fluid retention windows 2750. Where provided, the end sealing ridges 2714 provide a sealing function as described above. The surfaces 2713 of the main body portion, disposed between the protrusions 2728 and forming a surface defining the fluid-retention windows 2750, may be curved surfaces, e.g., when the main body portion is cylindrical. Alternatively, the surfaces 2713 may be flat. In alternative embodiments, the size, spacing density, and alignment patterns of the facets 2718 can be modified extensively.

The exemplary embodiments of FIGS. 21-28 have been described with reference to rounded knobs or square facets as supporting the flexible sample tube, although protrusions of any geometrical configuration may be used. Other geometrical configurations for the protrusions are also contemplated, such as conical or frustoconical spikes, tectiform or truncated tectiform protrusions, cylindrical protrusions, pyramidal or truncated pyramidal protrusions, hemiellipsoidal protrusions, and so forth, as well as any combinations thereof. Likewise, the size, spacing, and pattern of the protrusions can be varied. Where the sample is to be imaged, the size and spacing can be selected in accordance with the imaging field of view and other factors.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

What is claimed is:

1. A method of separating and axially expanding buffy coat constituents of a blood sample, comprising:
   introducing the blood sample into a flexible sample tube, the sample tube having an elongate sidewall having a first cross-sectional inner diameter;
   introducing an elongate, rigid, volume-occupying float into the flexible sample tube, said float having a specific gravity intermediate that of red blood cells and plasma; said float comprising:
      a main body portion; and
      one or more support members protruding from the main body portion to engage and support the sidewall of the sample tube;
      wherein said main body portion and said support members of the float having a cross-sectional diameter less than said first inner diameter of the tube when the sample tube is expanded;
      wherein said main body portion together with an axially aligned portion of said sidewall defines an annular volume therebetween; and
      wherein said support members traverse said annular volume to produce one or more analysis areas;
   creating a pressure differential such that the pressure inside the tube exceeds the pressure outside the tube to cause a resilient enlargement of the sidewall to a second diameter, said second diameter being sufficiently large to permit axial movement of the float in the tube;
   moving said float into axial alignment with at least the buffy coat constituents of the blood sample; and
   thereafter removing the pressure applied to the inside of the tube to cause the tube sidewall to return to said first diameter, thereby capturing the float and trapping the buffy coat constituents in the analysis area.

2. The method of claim 1, wherein the pressure differential is created by increasing the pressure inside the tube.

3. The method of claim 1, wherein the pressure differential is created by applying a vacuum to the outside of the tube.

4. The method of claim 1, wherein said float is introduced into the flexible sample tube before the blood is introduced therein.

5. The method of claim 1, wherein said blood sample is introduced into the flexible sample tube before the float is introduced therein.

6. The method of claim 1, wherein the blood sample comprises anticoagulated whole blood.

7. The method of claim 1, wherein the flexible sample tube comprises a closed first end and an open second end to receiver a closure device and the float.

8. The method of claim 1, wherein the flexible tube is sized to receive a blood sample of approximately ten milliliters in volume.

9. The method of claim 1, wherein the float is further moved into axial alignment with at least one of a portion of a separated red blood cell layer and a portion of a separated plasma layer.

10. The method of claim 1, wherein the float includes opposite axial ends which are tapered in an axial direction.

11. The method of claim 1, wherein the one or more support members include one or more annular ridges.

12. The method of claim 1, wherein the one or more support members include two annular ridges.

13. The method of claim 12, wherein the annular ridges are disposed at opposite axial ends of the float.

14. The method of claim 1, wherein the one or more support members comprises a helical ridge.

15. The method of claim 1, wherein the one or more support members include a plurality of radially spaced-apart splines.

16. The method of claim 15, wherein the splines are aligned parallel to an axis of the float.

17. The method of claim 1, wherein the one or more support members include a plurality of radially spaced-apart splines intersecting with a plurality of axially spaced-apart splines.

18. The method of claim 1, wherein the one or more support members include a plurality of raised protrusions spaced over the surface of the main body portion.

19. The method of claim 18, wherein the protrusions are selected from rounded bumps and faceted bumps.

20. An apparatus for separation and analysis of buffy coat constituents of a blood sample, comprising:
   a flexible sample tube for holding the sample, the sample tube having an elongate sidewall of a first cross-sectional inner diameter;
   an elongate, rigid, volume-occupying float having a specific gravity intermediate that of red blood cells and plasma, said float comprising:
      a main body portion; and
      one or more support members protruding from the main body portion to engage and support the sidewall of the sample tube;
      wherein said main body portion and said support members have a cross-sectional diameter less than said first inner diameter of the tube when the sample tube is expanded;
      wherein said main body portion together with an axially aligned portion of said sidewall define an annular volume therebetween; and
      wherein said support members traverse said annular volume to produced one or more analysis areas; and
   a vacuum source operatively connected to an exterior of the sidewall;
   wherein said sidewall is resiliently expandable to a second diameter in response to the application of a vacuum to the exterior of the sidewall, said second diameter being sufficiently large to permit axial movement of the float in the tube during centrifugation.

* * * * *